(12) United States Patent
Kawamura et al.

(10) Patent No.: US 7,939,100 B2
(45) Date of Patent: *May 10, 2011

(54) TULOBUTEROL ADHESIVE PATCH

(75) Inventors: Naohisa Kawamura, Kasukabe (JP);
Hidenori Sawada, Kasukabe (JP);
Yoshiki Sugizaki, Kasukabe (JP);
Takashi Saitoh, Kasukabe (JP)

(73) Assignee: Saitama Daiichi Pharmaceutical Co., Ltd., Saitama (JP)

( * ) Notice: Subject to any disclaimer, the term of this patent is extended or adjusted under 35 U.S.C. 154(b) by 904 days.

This patent is subject to a terminal disclaimer.

(21) Appl. No.: 10/585,168

(22) PCT Filed: Dec. 21, 2004

(86) PCT No.: PCT/JP2004/019078
§ 371 (c)(1),
(2), (4) Date: Jun. 30, 2006

(87) PCT Pub. No.: WO2005/067910
PCT Pub. Date: Jul. 28, 2005

(65) Prior Publication Data
US 2007/0154535 A1    Jul. 5, 2007

(30) Foreign Application Priority Data

Jan. 20, 2004 (JP) ................. 2004-011384

(51) Int. Cl.
*A61F 13/02* (2006.01)
*A61L 15/16* (2006.01)
*A61F 13/00* (2006.01)
*A61K 9/70* (2006.01)
*A61K 31/15* (2006.01)
*A01N 33/26* (2006.01)

(52) U.S. Cl. .................. 424/448; 424/449; 514/649

(58) Field of Classification Search .................. None
See application file for complete search history.

(56) References Cited

U.S. PATENT DOCUMENTS

| 5,185,212 | A | * | 2/1993 | Spada et al. | 428/483 |
| 5,254,348 | A | * | 10/1993 | Hoffmann et al. | 424/449 |
| 5,866,157 | A | * | 2/1999 | Higo et al. | 424/448 |
| 5,948,433 | A | * | 9/1999 | Burton et al. | 424/448 |
| 6,632,906 | B1 | * | 10/2003 | Kamiyama | 526/316 |

FOREIGN PATENT DOCUMENTS

| JP | 64-036669 | | 2/1989 |
| JP | 01-178566 | | 7/1989 |
| JP | 05-194202 | | 8/1993 |
| JP | 05-310559 | | 11/1993 |
| JP | 06-108033 | | 4/1994 |
| JP | 07-238203 | | 9/1995 |
| JP | 09-301854 | | 11/1997 |
| JP | 11-228395 | | 8/1999 |
| JP | 2002-363069 | | 12/2002 |
| JP | 2003-300868 | | 10/2003 |
| JP | 2003-313122 | | 11/2003 |
| WO | WO 86/06281 | * | 11/1986 |
| WO | WO97/14411 | | 4/1997 |
| WO | WO 9714411 | * | 4/1997 |
| WO | WO2004/112760 | | 12/2004 |

* cited by examiner

*Primary Examiner* — Sharmila Gollamudi Landau
*Assistant Examiner* — Nicoletta Kennedy
(74) *Attorney, Agent, or Firm* — Ohlandt, Greeley, Ruggiero & Perle, L.L.P.

(57) ABSTRACT

The present invention provides a tulobuterol adhesive patch comprising (a) a support, (b) an acrylic pressure-sensitive adhesive layer containing the percutaneously absorbing drug tulobuterol and if necessary a lipophilic oily plasticizer, and (c) a release liner, laminated in that order, wherein the acrylic pressure-sensitive adhesive is a copolymer obtained by copolymerizing an acrylic monomer which is acetoacetoxyalkyl (meth) acrylate with one or more other vinyl monomers, to yield a tulobuterol adhesive patch with excellent release and skin permeability of tulobuterol from the pressure-sensitive adhesive layer, low skin irritation and excellent safety.

1 Claim, No Drawings

TULOBUTEROL ADHESIVE PATCH

TECHNICAL FIELD

The present invention relates to a tulobuterol adhesive patch comprising as the active ingredient tulobuterol, which exhibits a bronchodilating effect, and employing an acrylic-based pressure-sensitive adhesive composed of a copolymer containing acetoxyalkyl (meth)acrylate as a constituent monomer in the pressure-sensitive adhesive layer.

BACKGROUND ART

Adhesive patches are known which contain tulobuterol as a selective stimulant of sympathetic nerve β2 receptors in a pressure-sensitive adhesive layer composed mainly of a synthetic rubber-based pressure-sensitive adhesive (for example, see Patent document 1). There are also known adhesive patches containing tulobuterol in a pressure-sensitive adhesive layer composed mainly of an acrylic-based pressure-sensitive adhesive (for example, see Patent document 2).

In an adhesive patch containing tulobuterol in a synthetic rubber-based pressure-sensitive adhesive where the crystals of tulobuterol are dispersed in the pressure-sensitive adhesive layer, sustained release of the tulobuterol from the pressure-sensitive layer is therefore achieved, yet not without problems such as poor start in release and inadequate release amount. Also, while the start in release is improved with an adhesive patch employing an acrylic-based pressure-sensitive adhesive, the lack of sustained release is a problem.

In other words, pressure-sensitive adhesives used in conventional tulobuterol adhesive patches have poor compatibility with the drug and additives, such that the drug must be added in an amount above the saturation concentration and deposition of crystals of the drug in the pressure-sensitive adhesive layer can occur, possibly resulting in unsatisfactory drug release and adhesion to skin.

There are also known pressure-sensitive adhesives wherein a copolymer obtained by copolymerizing acetoacetoxyalkyl (meth)acrylate and another vinyl monomer is crosslinked using a polyamine compound or isocyanate compound (for example, see Patent documents 3 and 4). However, no literature can be found describing an adhesive patch obtained by adding a percutaneously absorbing drug to an acrylic-based pressure-sensitive adhesive layer composed of a copolymer comprising acetoacetoxyalkyl (meth)acrylate as one of the constituent monomers.

[Patent document 1] WO97/14411
[Patent document 2] Japanese Unexamined Patent Publication HEI No. 11-228395
[Patent document 3] Japanese Unexamined Patent Publication HEI No. 6-108033
[Patent document 4] Japanese Unexamined Patent Publication HEI No. 7-238203

DISCLOSURE OF THE INVENTION

Problems to be Solved by the Invention

The present invention provides a tulobuterol adhesive patch with excellent tulobuterol release from the pressure-sensitive adhesive layer and excellent skin permeability, as well as superior safety with minimal skin irritation.

Means for Solving the Problems

As a result of much diligent research directed toward solving the problems referred to above, the present inventors have discovered that an acrylic-based pressure-sensitive adhesive comprising an acetoacetoxyalkyl (meth)acrylate and one or more other vinyl monomers that are copolymerizable with the acetoacetoxyalkyl (meth)acrylate has very high compatibility with tulobuterol and lipophilic oil plasticizers. As a result, it was confirmed that adding tulobuterol and in some cases a lipophilic oil plasticizer to the aforementioned acrylic-based pressure-sensitive adhesive yields a tulobuterol adhesive patch having excellent release of tulobuterol from the pressure-sensitive adhesive layer and excellent skin permeability, as well as superior safety with minimal skin irritation, and the present invention was thereupon completed.

EFFECT OF THE INVENTION

The tulobuterol adhesive patch of the invention prepared by adding tulobuterol as a percutaneous absorbing agent, and if necessary also a lipophilic oil plasticizer, to an acrylic-based pressure-sensitive adhesive comprising a copolymer obtained by copolymerizing an acetoacetoxyalkyl (meth) acrylate with one or more other vinyl monomers, exhibits excellent adhesive properties such as cohesive force, pressure-sensitive adhesive force and autohesion, as well as excellent release of tulobuterol from the adhesive patch and excellent skin permeability. Moreover, these effects of the tulobuterol adhesive patch of the invention are superior to those of an adhesive patch obtained by combining tulobuterol with a pressure-sensitive adhesive layer composed of a known acrylic-based pressure-sensitive adhesive or a synthetic rubber-based pressure-sensitive adhesive.

In addition, the safety of the tulobuterol adhesive patch of the invention, based on evaluation using a skin primary irritation test with rabbits, is also superior to that of a tulobuterol adhesive patch wherein tulobuterol is combined with a synthetic rubber-based pressure-sensitive adhesive as evaluated based on low skin irritation, for instance.

Since the autohesion tends to be too strong with a rubber-based pressure-sensitive adhesive it has been necessary to add a low molecular weight polymer or the like to adjust the autohesion, but the adhesive patch of the invention is superior in that it requires no such addition. Also, a conventionally used acrylate-based adhesive patch requires a crosslinking agent in order to achieve sufficient adhesive strength, but polyamine-based compounds and isocyanate-based compounds used as crosslinking agents have toxicity and can affect the formulated drugs. The adhesive patch of the invention is superior in this aspect since it requires no addition of a crosslinking agent.

The non-aqueous pressure-sensitive adhesive obtained by copolymerizing a (meth) acrylic monomer with an acetoacetyl group and another vinyl monomer with no acetoacetyl group in a non-aqueous solvent according to the present invention is kneaded together with tulobuterol and a plasticizer, by which the tulobuterol dissolves in the residual non-aqueous solvent and plasticizer and is thoroughly and homogeneously mixed therewith. When the mixture is coated onto a support or release film and heated to dryness, the acetoacetyl groups self-crosslink to form a reticulate structure, wherein the tulobuterol and plasticizer are present in a dissolved state in the pressure-sensitive adhesive. A large amount of an oily substance may also be added to the reticulate structure formed by self-crosslinking of the acetoacetyl groups. The amount of oily substance in the pressure-sensitive adhesive layer can thus be adjusted within a wide range.

By increasing or decreasing the amount of (meth)acrylic monomer with acetoacetyl groups as the starting material, it is possible to vary the degree of self-crosslinking of the pressure-sensitive adhesive and adjust the adhesive and cohesive force. Moreover, by adjusting the amounts of lipophilic oily substances such as plasticizers, percutaneous absorption accelerators and drug solubilizers added to the pressure-sensitive adhesive layer, it is possible to provide a suitable level of adhesive and cohesive force.

Best Mode For Carrying out the Invention

The adhesive patch of the invention is an adhesive patch comprising (a) a support, (b) an acrylic pressure-sensitive adhesive layer containing the percutaneously absorbing drug tulobuterol and if necessary a lipophilic oily plasticizer, and (c) a release liner, laminated in that order, wherein the acrylic pressure-sensitive adhesive layer is an acrylic pressure-sensitive adhesive layer comprising a copolymer obtained by copolymerizing an acetoacetoxyalkyl (meth) acrylate and one or more other vinyl monomers.

The thickness of the support used for the adhesive patch of the invention will normally be 5-400 μm and is preferably 5-250 μm. An elastic support is preferred, although it may be non-elastic so long as it is flexible, and the material used must be impermeable to the drug, but may be either a support with a single-layer structure or a support having a laminated structure of a plurality of different materials. When the support has a single-layer structure, it is preferred to use a plastic film such as polyethylene, polyester, polypropylene, polyvinyl chloride, polycarbonate or polyurethane, or a metal film, and the surface of the film may also be silicon-treated. The support may be colorless and transparent, or colored with a white or skin color, and a colored support having a white or skin color may be obtained by coating the support surface with a dye or by uniformly kneading a dye or pigment with the support.

When a support with a laminated structure is used, it is sufficient if at least one of the layers is impermeable to the drug, and the laminated film may be obtained by laminating one or more materials selected from among polyethylene, polyesters, polyurethanes or polypropylene nonwoven fabrics, woven fabrics, knitted fabrics, paper sheets or metal films, onto the aforementioned single-layer support film.

The release liner used for the adhesive patch of the invention serves for protection of the pressure-sensitive adhesive layer, and the release liner is peeled from the adhesive patch before attaching the adhesive patch onto the intended area of the skin. The thickness of the release liner will normally be 15-200 μm, and is preferably 40-100 μm. The release liner used may be of any material which can be easily peeled from the pressure-sensitive adhesive layer and which is impermeable to the drug. For example, it may be a single-layer film made of a material selected from among plastic films such as polyethylene, polyvinyl chloride, polyester or polypropylene, or a paper sheet, metal film or fabric, or it may be a laminated body of two or more different materials. The surfaces of such films may also be silicon-treated.

The percutaneously absorbing drug tulobuterol of the invention is formulated in the pressure-sensitive adhesive layer in a dissolved state, and it may be formulated in a content of less than the saturation solubility with respect to the total of the pressure-sensitive adhesive, plasticizer and other additives, but the content is preferably 1-10 wt % of the total amount of the pressure-sensitive adhesive layer, although this may differ depending on the type of pressure-sensitive adhesive and the types of additives.

As plasticizers to be added to the pressure-sensitive adhesive layer there are preferred lipophilic oils, and as examples there may be mentioned fatty acid esters having 6-18 carbon atoms, dibasic acid esters having 6-10 carbon atoms, higher alcohols having 10-18 carbon atoms and castor oil. As examples of fatty acid esters having 6-18 carbon atoms there may be mentioned higher fatty acid esters such as hexyl laurate, isopropyl myristate and isopropyl palmitate, or glycerin fatty acid esters such as medium chain fatty acid triglycerides.

As examples of dibasic acid esters having 6-10 carbon atoms there may be mentioned diisopropyl adipate, dioctyl adipate, diethyl adipate, diisopropyl sebacate and diethyl sebacate. As examples of higher alcohols having 10-18 carbon atoms there may be mentioned hexyldecanol, myristyl alcohol, lauryl alcohol, oleyl alcohol and octyldodecanol.

The plasticizer used may be one or more appropriately selected from among the aforementioned lipophilic oils, used either alone or in admixture, with isopropyl myristate being most preferred. These plasticizers are highly suitable because of their plasticizing effects on pressure-sensitive adhesives and their role as tulobuterol solubilizers with percutaneous absorption accelerating effects for tulobuterol. These plasticizers are liquid at room temperature (1-30° C.). The content of the plasticizer may be up to about 40 wt % of the total weight of the pressure-sensitive adhesive layer and preferably up to about 35 wt % of the total weight of the pressure-sensitive adhesive layer, because addition at greater than 45 wt % may render it impossible to retain the oil in the pressure-sensitive adhesive layer and the oil may separate from the pressure-sensitive adhesive layer.

The pressure-sensitive adhesive used in the pressure-sensitive adhesive layer of the adhesive patch of the invention is preferably an acrylic-based pressure-sensitive adhesive comprising a copolymer obtained by copolymerizing an acetoacetoxyalkyl (meth) acrylate and one or more vinyl monomers that are copolymerizable with the acetoacetoxyalkyl (meth) acrylate.

Acetoacetoxyalkyl (meth)acrylates include those wherein one of the hydroxyl groups of an alkyleneglycol is acylated with an acetoacetyl group and another hydroxyl group is acylated with acrylic acid or methacrylic acid, and examples include acetoacetoxyalkyl (meth)acrylates selected from among 2-acetoacetoxyethyl methacrylate and 2-acetoacetoxyethyl acrylate, although 2-acetoacetoxyethyl methacrylate is most preferred. The content of the acetoacetoxyalkyl (meth)acrylate is preferably about 5-50 wt % and more preferably about 10-45 wt %, based on 100 as the total weight of the copolymer.

As the vinyl monomer for copolymerization with the acetoacetoxyalkyl (meth) acrylate there may be used any compound having in the molecule a double bond that copolymerizes with acetoacetoxyalkyl (meth)acrylates, and for example, there may be used one or more vinyl monomers selected from the group consisting of (meth)acrylic acid alkyl esters with 1-12 carbon atoms in the alkyl group, functional monomers having in the molecule a functional group such as hydroxyl, amide and alkoxyalkyl, and glycol (meth)acrylates such as polyalkyleneglycol di(meth)acrylate.

As specific (meth) acrylic acid alkyl esters with 1-12 carbon atoms in the alkyl group there may be mentioned methyl (meth)acrylate, ethyl (meth)acrylate, propyl methacrylate, butyl methacrylate, 2-ethylhexyl methacrylate, octyl methacrylate and dodecyl methacrylate. As specific functional monomers having a functional group in the molecule there may be mentioned 2-methoxyethylmethacrylate, di-acetone-acrylamide and 2-hydroxyethyl methacrylate. As specific glycol (meth)acrylates there may be mentioned diethyleneglycol di(meth)acrylate, triethyleneglycol di(meth)acrylate, triethyleneglycol di(meth)acrylate and tetraethyleneglycol di(meth)acrylate.

The copolymerization between the acetoacetoxyalkyl (meth) acrylate and another vinyl monomer may be accomplished in the same manner as in the process for production of an acrylic-based pressure-sensitive adhesive using a polymerization initiator such as a peroxide compound or azo-compound. The acrylic-based pressure-sensitive adhesive used for the invention may be an non-aqueous adhesive obtained by dissolving the copolymer in an organic solvent, or an aqueous emulsion-type adhesive obtained by dispersing the polymer in an aqueous solvent together with a low skin-irritating surfactant.

As examples of low skin-irritating surfactants to be combined with an aqueous emulsion-type adhesive, there may be mentioned one or more types of surfactants selected from among anionic surfactants such as sodium lauryl sulfate and sodium dodecylbenzenesulfonate, cationic surfactants, nonionic surfactants such as polyoxyethylene lauryl ether and polyoxyethylene oleyl ether, and peptide-type surfactants such as surfactin, any of which may be used alone or in mixtures.

The solvent used for a non-aqueous adhesive to be employed in the aforementioned pressure-sensitive adhesive may be an organic solvent which volatilizes in the heat drying step during production of the adhesive patch. As examples of such organic solvents there may be mentioned hydrocarbons such as toluene, xylene, benzene, cyclohexane and n-hexane, lower fatty acid esters such as ethyl acetate, propyl acetate, butyl acetate and ethyl propionate, ketones such as acetone, methyl ethyl ketone and cyclohexanone and ethers such as isopropylether, di-butylether, tetrahydrofuran and dioxane. The solvent used for an aqueous emulsion-type adhesive may be any one which dissolves in water.

The pressure-sensitive adhesive layer of the adhesive patch of the invention may also contain additives such as tulobuterol solubilizers, absorption accelerators, tackifiers such as ester gums, aromatics and coloring agents, as desired in addition to the pressure-sensitive adhesive, the percutaneously absorbing drug tulobuterol and the plasticizer. The tulobuterol solubilizer used may be any solvent that dissolves tulobuterol and produces no skin irritation. For example, there may be used lower alcohols such as ethanol, propanol and isopropanol, medium chain alcohols such as hexanol and octanol, polyhydric alcohols such as glycerin, ethylene glycol and diethylene glycol, higher fatty acid esters, polyvinyl alcohol, N-methylpyrrolidone, crotamiton and the like, which may be used as solubilizers alone or in mixtures of two or more.

As examples of tulobuterol percutaneous absorption accelerators there may be mentioned aliphatic acid esters such as isopropyl myristate, isopropyl palmitate and diethyl adipate, aliphatic acid polyhydric alcohol esters such as caprylic acid monoglyceride, caprylic acid triglyceride and sorbitan fatty acid esters, and terpenes such as 1-menthol, peppermint oil and limonene.

As examples of other additives there may be mentioned silicon compounds such as silicic anhydride and light silicic anhydride, cellulose derivatives such as ethyl cellulose, methyl cellulose, sodium carboxymethylcellulose, hydroxypropylcellulose and hydroxypropylmethyl cellulose, water-soluble polymers such as polyvinyl alcohol, antioxidants such as dibutylhydroxytoluene, or kaolin, titanium oxide and the like.

The process for production of the tulobuterol adhesive patch of the invention comprises combining a pressure-sensitive adhesive, tulobuterol and if desired a plasticizer and additives to obtain a tulobuterol-dissolved solution, which is evenly coated onto the surface of a release liner to a thickness of 15-80 μm of post-drying pressure-sensitive adhesive layer and heated to dryness, after which a support is attached onto the surface of the pressure-sensitive adhesive and the laminate is cut to a prescribed size to obtain a tulobuterol adhesive patch according to the invention. Alternatively, a pressure-sensitive adhesive may be first coated and dried onto a support to form a pressure-sensitive adhesive layer which is then attached to a release liner and cut to a prescribed size to produce a tulobuterol adhesive patch according to the invention.

EXAMPLES

Examples and test examples will now be described for a more detailed explanation of the non-aqueous acrylic-based pressure-sensitive adhesive for a medical percutaneous absorption tape formulation, and the medical percutaneous absorption tape formulation, according to the present invention, with the understanding that these examples are not limitative on the invention.

Pressure-Sensitive Adhesive Production Example

Production of Non-aqueous Acrylic-based Pressure-sensitive Adhesive

A monomer solution was prepared by uniformly dissolving 158 g of 2-ethylhexyl acrylate, 35.1 g of 2-acetoacetoxyethyl methacrylate, 76.2 g of methyl methacrylate, 80.3 g of diacetoneacrylamide and 1.0 g of tetraethyleneglycol dimethacrylate. After charging 100 g of the monomer solution into a 2-liter four-necked flask provided with a Dimroth condenser, thermometer, nitrogen gas inlet tube and stirrer, 350 g of ethyl acetate was added as a solvent. The temperature was increased to 75° C. while blowing in nitrogen gas at a flow rate of 100 ml/min, and after maintaining a temperature of 75° C. for 30 minutes, 0.35 g of benzoyl peroxide was dissolved in 5 g of ethyl acetate and added as an initiator, and the external temperature was set to 85° C. After confirming reflux of the solvent, the remaining monomer was continuously charged in over a 3 hour period. From one hour after starting continuous charging of the monomer solution, 500 g of ethyl acetate was continuously charged in over a 3 hour period. After charging in ethyl acetate and then continuing to stir for 12 hours, 0.5 g of benzoyl peroxide was charged in as additional catalyst and the mixture was heat treated for 12 hours and then cooled to produce a solution of a non-aqueous acrylic-based pressure-sensitive adhesive.

Example 1

A 35.69 g portion of the non-aqueous acrylic-based pressure-sensitive adhesive produced in the pressure-sensitive adhesive production example was weighed out into a screw cap bottle, and then 3.0 g of isopropyl myristate and 1.5 g of tulobuterol were each weighed out and stirred therewith for one hour. The obtained mixture was applied by a coating tester (LTE-S, Wener Mathis) on a polyester film to form a layer with post-drying weight of 20 mg/10 cm$^2$, dried and covered with the silicone-treated side of a polyester release liner that had been silicone-treated on one side, in contact with the pressure-sensitive adhesive, to obtain a tulobuterol adhesive patch for Example 1 containing 10 wt % tulobuterol and 20 wt % isopropyl myristate in the pressure-sensitive adhesive layer.

Example 2

A tulobuterol adhesive patch for Example 2 containing 10 wt % tulobuterol in the pressure-sensitive adhesive layer was obtained in the same manner as Example 1, except that 1.5 g of tulobuterol and 38.69 g of the non-aqueous acrylic-based pressure-sensitive adhesive produced in the pressure-sensitive adhesive production example were used, and no isopropyl myristate was used.

Example 3

The same method as in Example 1 was carried out using 40.0 g of the non-aqueous acrylic-based pressure-sensitive adhesive produced in the pressure-sensitive adhesive production example, 0.5 g of tulobuterol and 3.0 g of isopropyl myristate, to form a layer with weight of 67 mg/10 cm$^2$ and to obtain a tulobuterol adhesive patch for Example 3 containing 3 wt % tulobuterol and 20 wt % isopropyl myristate in the pressure-sensitive adhesive layer.

Example 4

The same method as in Example 3 was carried out using 41.5 g of the non-aqueous acrylic-based pressure-sensitive adhesive produced in the pressure-sensitive adhesive production example, 0.5 g of tulobuterol and 1.5 g of isopropyl myristate, to obtain a tulobuterol adhesive patch for Example 4 containing 3 wt % tulobuterol and 10 wt % isopropyl myristate in the pressure-sensitive adhesive layer.

Example 5

The same method as in Example 3 was carried out using 37.75 g of the non-aqueous acrylic-based pressure-sensitive adhesive produced in the pressure-sensitive adhesive production example, 0.5 g of tulobuterol and 5.25 g of isopropyl myristate, to obtain a tulobuterol adhesive patch for Example 5 containing 3 wt % tulobuterol and 35 wt % isopropyl myristate in the pressure-sensitive adhesive layer.

Example 6

The same method as in Example 3 was carried out using 40.0 g of the non-aqueous acrylic-based pressure-sensitive adhesive produced in the pressure-sensitive adhesive production example, 0.5 g of tulobuterol and 3.0 g of diethyl sebacate, to obtain a tulobuterol adhesive patch for Example 6 containing 3 wt % tulobuterol and 20 wt % diethyl sebacate in the pressure-sensitive adhesive layer.

Example 7

The same method as in Example 3 was carried out using 38.5 g of the non-aqueous acrylic-based pressure-sensitive adhesive produced in the pressure-sensitive adhesive production example, 0.5 g of tulobuterol and 4.5 g of diethyl sebacate, to obtain a tulobuterol adhesive patch for Example 7 containing 3 wt % tulobuterol and 30 wt % diethyl sebacate in the pressure-sensitive adhesive layer.

Example 8

The same method as in Example 3 was carried out using 40.0 g of the non-aqueous acrylic-based pressure-sensitive adhesive produced in the pressure-sensitive adhesive production example, 0.5 g of tulobuterol and 3.0 g of isopropyl palmitate, to obtain a tulobuterol adhesive patch for Example 8 containing 3 wt % tulobuterol and 20 wt % isopropyl palmitate in the pressure-sensitive adhesive layer.

Example 9

The same method as in Example 3 was carried out using 40.0 g of the non-aqueous acrylic-based pressure-sensitive adhesive produced in the pressure-sensitive adhesive production example, 0.5 g of tulobuterol and 3.0 g of medium chain fatty acid triglycerides, to obtain a tulobuterol adhesive patch for Example 9 containing 3 wt % tulobuterol and 20 wt % medium chain fatty acid triglycerides in the pressure-sensitive adhesive layer.

Example 10

The same method as in Example 3 was carried out using 40.0 g of the non-aqueous acrylic-based pressure-sensitive adhesive produced in the pressure-sensitive adhesive production example, 0.5 g of tulobuterol and 3.0 g of castor oil, to obtain a tulobuterol adhesive patch for Example 10 containing 3 wt % tulobuterol and 20 wt % castor oil in the pressure-sensitive adhesive layer.

Example 11

The same method as in Example 3 was carried out using 40.0 g of the non-aqueous acrylic-based pressure-sensitive adhesive produced in the pressure-sensitive adhesive production example, 0.5 g of tulobuterol and 3.0 g of hexyldecanol, to obtain a tulobuterol adhesive patch for Example 11 containing 3 wt % tulobuterol and 20 wt % hexyldecanol in the pressure-sensitive adhesive layer.

Comparative Example 1

The same method as in Example 1 was carried out using a commercially available non-aqueous acrylic-based pressure-sensitive adhesive (Nissetsu PE300, Nippon Carbide, pressure-sensitive adhesive composition: 2-ethylhexyl acrylate:2-hydroxyethyl acrylate:vinyl acetate=17:2:1) as the pressure-sensitive adhesive, to obtain a tulobuterol adhesive patch for Comparative Example 1 containing 10 wt % tulobuterol and 20 wt % isopropyl myristate in the pressure-sensitive adhesive layer.

Comparative Example 2

The same method as in Example 2 was carried out using a commercially available non-aqueous acrylic-based pressure-sensitive adhesive (Nissetsu PE300, Nippon Carbide) as the pressure-sensitive adhesive, to obtain a tulobuterol adhesive patch for Comparative Example 2 containing 10 wt % tulobuterol in the pressure-sensitive adhesive layer.

Comparative Example 3

A commercially available tulobuterol adhesive patch, H Tape, employing a synthetic rubber-based pressure-sensitive adhesive, was used as the tulobuterol adhesive patch for Comparative Example 3.

Comparative Example 4

Polymerizing synthesis was carried out by the same method as in the pressure-sensitive adhesive production example, using a monomer composition of 90 g of 2-ethylhexyl acrylate, 90 g of n-butyl acrylate, 80.5 g of diacetoneacrylamide, 87.5 g of methyl methacrylate, and 0.3 g of diethyleneglycol dimethacrylate to produce an acrylic-based pressure-sensitive adhesive. This pressure-sensitive adhesive was used in the same manner as Example 1 to obtain a tulobuterol adhesive patch for Comparative Example 4 containing 10 wt % tulobuterol in the pressure-sensitive adhesive layer.

Test Example 1

Tulobuterol Release Test and Skin Permeability Test for Adhesive Patch

The tulobuterol adhesive patches of Examples 1-3 and the tulobuterol adhesive patches of Comparative Examples 1-3 were used for evaluation of the tulobuterol adhesive patch release properties and skin Permeabilities by the test methods described below.

1) Release Property Test Method

A test adhesive patch was attached to a skin sample extracted from a Yucatan micropig and allowed to stand under conditions of 32° C., 60% humidity. After 24 hours, the test adhesive patch was peeled off and the residual drug amount in the formulation was measured by HPLC. The residual drug amount was used in the following formula to calculate the drug release rate (%) from the adhesive patch.

[(Drug content before application−residual drug amount)/drug concentration before application]×100=Drug release rate (%)

2) Skin Permeability Test Method

Skin permeability tests were conducted with hairless mouse skin samples using the tulobuterol adhesive patches of Examples 1-2 and Comparative Examples 1-2, and with Wistar rat skin samples using the tulobuterol adhesive patches of Example 3 and Comparative Example 3.

2-1) Hairless Mouse Skin Sample Permeability Test Method

On the hairless mouse skin sample dermis side (receiver side) of a vertical diffusion cell there was placed 0.05 mol/L McIlvaine buffer (pH 7.4), while the tulobuterol adhesive patch was applied on the cuticle layer side (donor side). At different time points, the receiver solution was sampled and an equal amount of 0.05 mol/L McIlvaine buffer was added. The drug concentration in the sampled solution was assayed by HPLC, and the flux value (value of the skin permeation rate of the drug in a steady state), lag time (time until skin permeation rate in the steady state is reached) and 24-hour cumulative permeation were calculated.

The tulobuterol adhesive patches of Examples 1 and 2 and Comparative Examples 1 and 2 were used in the tests described above, producing the results shown in the following table (Table 1). Specifically, the formulation of Example 1, which was a tulobuterol adhesive patch having a pressure-sensitive adhesive layer obtained by combining tulobuterol and a plasticizer with an acrylic-based pressure-sensitive adhesive containing a 2-acetoacetoxyethyl methacrylate monomer according to the invention, was superior in terms of release rate, flux value, cumulative permeation and lag time, compared to Comparative Example 1 which was a tulobuterol adhesive patch having a pressure-sensitive adhesive layer obtained by combining tulobuterol and a plasticizer with a commercially available acrylic-based pressure-sensitive adhesive containing no 2-acetoacetoxyethyl methacrylate monomer. Also, the release rate, flux value, cumulative permeation and lag time of the tulobuterol adhesive patch of Example 2 of the invention, having a composition containing no plasticizer, were superior to the release rate, flux value, cumulative permeation and lag time of Comparative Example 2 having a composition containing no plasticizer.

TABLE 1

Drug release rates from tulobuterol adhesive patches and hairless mouse skin permeabilities

| Adhesive patch | Content (%) Isopropyl myristate | Content (%) Tulobuterol | Plaster weight mg/10 cm² | Release rate %/24 hr | Lag time hr | Flux µg/cm²/hr | Cumulative permeation µg/cm²/24 hr |
|---|---|---|---|---|---|---|---|
| Example 1 | 20 | 10 | 20 | 96.1 ± 0.3 | 0.17 ± 0.17 | 3.620 ± 0.057 | 29.40 ± 1.23 |
| Example 2 | 0 | 10 | 20 | 95.7 ± 0.8 | 2.31 ± 0.98 | 1.757 ± 0.398 | 17.71 ± 4.27 |
| Comp. Ex. 1 | 20 | 10 | 20 | 83.0 ± 0.4 | 1.10 ± 0.28 | 2.238 ± 0.008 | 20.98 ± 2.24 |
| Comp. Ex. 2 | 0 | 10 | 20 | 88.9 ± 0.2 | 5.14 ± 1.93 | 0.335 ± 0.133 | 3.30 ± 1.12 |

The plasticizer and drug amounts are shown as weight percentages with respect to 100 as the total weight of the pressure-sensitive adhesive layer 2-2) Wistar Rat Skin Sample Permeability Test Method Wister rat skin samples were used instead of hairless mouse skin samples for testing by the same method as in 2-1) above, and the flux values were determined.

The test described above was carried out using the tulobuterol adhesive patch of Example 3 obtained by combining tulobuterol with an acrylic-based pressure-sensitive adhesive containing a 2-acetoacetoxyethyl methacrylate monomer according to the invention, and the tulobuterol adhesive patch of Comparative Example 3 containing tulobuterol in a synthetic rubber-based pressure-sensitive adhesive, producing the results shown in Table 2.

TABLE 2

Wistar rat skin permeabilities from tulobuterol adhesive patches

| | Tulobuterol content (%) | Plaster weight (mg/10 cm²) | Flux (µg/cm²/hr) |
|---|---|---|---|
| Example 3 | 3 | 67 | 15.9 |
| Comp. Ex. 3 | 10 | 20 | 6.3 |

The results shown above indicate that the rat skin permeability of the adhesive patch obtained by combining tulobuterol with the 2-acetoacetoxyethyl methacrylate monomer-containing acrylic-based pressure-sensitive adhesive of Example 3 according to the invention was superior to the skin permeability of the tulobuterol adhesive patch of Comparative Example 3 obtained by combining tulobuterol with a synthetic rubber-based pressure-sensitive adhesive.

Test Example 2

Skin Irritation Test

The safety of the tulobuterol adhesive patch of Example 3 according to the invention and the tulobuterol adhesive patch of Comparative Example 3 was evaluated by a primary skin irritation test with rabbits.

1) Primary Skin Irritation Test Method (Rabbits)

Rabbit dorsal hair was shaved with an electric razor up until the day prior to the test. The formulation was applied onto the rabbit dorsum, impermeable greased paper was placed thereover, a pressure-sensitive adhesive bandage made of a non-woven fabric (Meshpore, product of Nichiban) was attached and fixed thereto, and the entire application site was covered with gauze and surrounded with a pressure-sensitive adhesive elastic bandage (Elastpore, product of Nichiban). After 24 hours, the test formulation was removed, the application site was lightly wiped with absorbent cotton wetted with lukewarm water, and the application site was observed after standing for 30 minutes. The application site was also observed 48 and 72 hours after application of the formulation, and scored based on the evaluation scale of Draize et al. shown below; the primary irritation index (P.I.I.) was calculated from the score at 24 and 72 hours after application.

Evaluation scale of Draize et al.

A: Erythema and Scabbing

No erythema: 0, very mild erythema: 1, notable erythema: 2, moderate to severe erythema: 3, severe erythema to mild scabbing: 4

B: Edema

No edema: 0, very mild edema: 1, mild edema: 2, moderate edema (approximately 1 mm swelling): 3, severe edema: 4

2) Test Evaluation

The tulobuterol adhesive patch of Example 3 according to the invention and the tulobuterol adhesive patch of Comparative Example 3 were used for a primary skin irritation test with rabbits by the method of Test Example 2 above, yielding the skin primary irritation indexes shown in Table 3. As a result, the tulobuterol adhesive patch of Example 3 according to the invention had lower skin irritation than the tulobuterol adhesive patch of Comparative Example 3.

TABLE 3

Skin primary irritation indexes of tulobuterol adhesive patches

|  | Skin primary irritation index |
|---|---|
| Example 3 | 1.25 |
| Comp. Ex. 3 | 2.19 |

Test Example 3

Pressure-sensitive Adhesive Property Test

The tulobuterol adhesive patches of Examples 1-11 according to the invention and the tulobuterol adhesive patches of Comparative Examples 1-4 were used for evaluation of the pressure-sensitive adhesive properties by the following (functional) test method from the three viewpoints of cohesive force, adhesive force and autohesion.

1) Pressure-sensitive Adhesive Property Test Method 1-1) Cohesive Force

The liner of the formulation was released and the adhesive side was contacted with the skin for evaluation based on the following criteria.

Evaluation Criteria

○: (Excellent) Cohesive force equivalent to commercially available indomethacin-containing tape preparation S and commercially available felbinac-containing tape preparation F, which employ natural rubber latex.

Δ: (Good) Cohesive force equivalent to commercially available ketoprofen-containing tape preparation M and commercially available flurbiprofen-containing tape preparation Y, which employ styrene-isoprene-styrene copolymer.

X: (Poor) Cohesive force inferior to commercially available products.

-: Cohesive force too low to evaluate (semi-solid state).

1-2) Adhesive Force

The liner of the formulation was released and the adhesive side was contacted with the skin for evaluation based on the following criteria.

Evaluation Criteria

○: (Excellent) Adhesive force equivalent to commercially available ketoprofen-containing tape preparation M and commercially available flurbiprofen-containing tape preparation Y, which employ styrene-isoprene-styrene copolymer.

Δ: (Good) Adhesive force equivalent to commercially available indomethacin-containing tape preparation S and commercially available felbinac-containing tape preparation F, which employ natural rubber latex.

X: (Poor) Adhesive force inferior to commercially available products.

—: Adhesive force too low to evaluate (semi-solid state).

1-3) Autohesion

The ease of release after attachment of the pressure-sensitive adhesive side of the formulation to itself was evaluated based on the following criteria.

Evaluation criteria

○: (Excellent) Release without resistance.

Δ: (Good) Release with only some resistance.

X: (Poor) Considerable resistance rendering release difficult.

2) Evaluation Results

The tulobuterol adhesive patches of Examples 1-11 according to the invention and the tulobuterol adhesive patches of Comparative Examples 1-4 were used for the pressure-sensitive adhesive property test described above. The results are shown in Table 4.

TABLE 4

Pressure-sensitive adhesive properties of tulobuterol adhesive patches

| Adhesive patch | Plasticizer content (%) | Tulobuterol content (%) | Plaster weight (mg/10 cm$^2$) | Presence of crystals | Cohesive force | Adhesive force | Autohesion |
|---|---|---|---|---|---|---|---|
| Example 1 | Isopropyl myristate: 20 | 10 | 20 | none | ○ | ○ | ○ |
| Example 2 | — | 10 | 20 | none | ○ | ○ | ○ |

TABLE 4-continued

Pressure-sensitive adhesive properties of tulobuterol adhesive patches

| Adhesive patch | Plasticizer content (%) | Tulobuterol content (%) | Plaster weight (mg/10 cm²) | Presence of crystals | Cohesive force | Adhesive force | Autohesion |
|---|---|---|---|---|---|---|---|
| Example 3 | Isopropyl myristate: 20 | 3 | 67 | none | ○ | ○ | ○ |
| Example 4 | Isopropyl myristate: 10 | 3 | 67 | none | ○ | ○ | ○ |
| Example 5 | Isopropyl myristate: 35 | 3 | 67 | none | ○ | ○ | ○ |
| Example 6 | Diethyl sebacate: 20 | 3 | 67 | none | ○ | ○ | ○ |
| Example 7 | Diethyl sebacate: 30 | 3 | 67 | none | ○ | ○ | ○ |
| Example 8 | Isopropyl palmitate: 20 | 3 | 67 | none | ○ | ○ | ○ |
| Example 9 | Medium chain fatty acid triglycerides: 20 | 3 | 67 | none | ○ | ○ | ○ |
| Example 10 | Castor oil: 20 | 3 | 67 | none | ○ | ○ | ○ |
| Example 11 | Hexyldecanol: 20 | 3 | 67 | none | ○ | ○ | ○ |
| Comp. Ex. 1 | Isopropyl myristate: 20 | 10 | 20 | none | X | — | — |
| Comp. Ex. 2 | — | 10 | 20 | none | X | — | — |
| Comp. Ex. 3 | — | 10 | 20 | crystals | ○ | Δ | X |
| Comp. Ex. 4 | Isopropyl myristate: 20 | 10 | 20 | none | X | — | — |

— Insufficient cohesive force for evaluation

The plasticizer and drug amounts are shown as weight percentages with respect to 100 as the total weight of the pressure-sensitive adhesive layer From the three viewpoints of cohesive force, adhesive force and autohesion, the tulobuterol adhesive patches of Examples 1-11 according to the invention obtained by combining tulobuterol with an acrylic-based pressure-sensitive adhesive comprising a copolymer containing a 2-acetoacetoxyethyl methacrylate as a monomer component were superior to the tulobuterol adhesive patches of Comparative Examples 1, 2 and 4 obtained by combining tulobuterol with an acrylic-based pressure-sensitive adhesive comprising a copolymer containing no 2-acetoacetoxyethyl methacrylate as a monomer component. The tulobuterol adhesive patches of Examples 1-11 according to the invention were also superior from the standpoint of adhesive force and autohesion, while exhibiting the same level of cohesive force as the tulobuterol adhesive patch of Comparative Example 3 obtained by combining tulobuterol with a synthetic rubber-based pressure-sensitive adhesive.

INDUSTRIAL APPLICABILITY

By using a copolymer obtained by copolymerization of an acrylic monomer which is acetoacetoxyalkyl (meth) acrylate and one or more other vinyl monomers, it is possible to provide a highly safe tulobuterol adhesive patch with excellent adhesive force, cohesive force and autohesion, as well as excellent release of tulobuterol from the pressure-sensitive adhesive layer, excellent skin permeability and low skin irritation, as a pressure-sensitive adhesive.

The invention claimed is:

1. A tulobuterol adhesive patch which comprises:
   (a) a support;
   (b) a pressure-sensitive adhesive layer; and
   (c) a release liner laminated in that order,
   wherein said pressure-sensitive adhesive layer (b) contains:
      isopropyl myristate as a plasticizer, wherein the amount of the plasticizer is 10-35 wt % of the total weight of the pressure-sensitive adhesive layer;
      a tulobuterol as a percutaneous absorbing agent, wherein the amount of tulobuterol is 1-10 wt % of the total weight of the pressure-sensitive adhesive layer; and
      an acrylic-based pressure-sensitive adhesive agent which is a copolymer of 2-acetoacetoxyethyl (meth) acrylate, diacetoneacrylamide, tetraethyleneglycol dimethacrylate, 2-ethylhexylacrylate and methylmethacrylate, wherein the amount of acetoacetoxyalkyl (meth)acrylate is 10-45 wt % of the total weight of the acrylic pressure-sensitive adhesive agent.

* * * * *

UNITED STATES PATENT AND TRADEMARK OFFICE
CERTIFICATE OF CORRECTION

| | | |
|---|---|---|
| PATENT NO. | : 7,939,100 B2 | Page 1 of 1 |
| APPLICATION NO. | : 10/585168 | |
| DATED | : May 10, 2011 | |
| INVENTOR(S) | : Naohisa Kawamura et al. | |

It is certified that error appears in the above-identified patent and that said Letters Patent is hereby corrected as shown below:

Please change the assignee name to Nipro Patch Co., Ltd.

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,939,100 B2
APPLICATION NO. : 10/585168
DATED : May 10, 2011
INVENTOR(S) : Naohisa Kawamura et al.

Page 1 of 1

It is certified that error appears in the above-identified patent and that said Letters Patent is hereby corrected as shown below:

Title Page, Item (73) Assignee, please change the assignee name to Nipro Patch Co., Ltd.

This certificate supersedes the Certificate of Correction issued June 14, 2011.

Signed and Sealed this
Twelfth Day of July, 2011

David J. Kappos
*Director of the United States Patent and Trademark Office*